United States Patent [19]
Lopa et al.

[11] Patent Number: 6,050,099
[45] Date of Patent: Apr. 18, 2000

[54] APPARATUS FOR DISPENSING LIQUID ON A WEARER'S HEAD

[76] Inventors: Frank Lopa, 94 Grayson St., Staten Island, N.Y. 10306; John Giammona, 202 Bay 46th St., Brooklyn, N.Y. 11214

[21] Appl. No.: 09/157,265

[22] Filed: Sep. 21, 1998

[51] Int. Cl.[7] .................................................. F25D 23/12
[52] U.S. Cl. .............................. 62/259.3; 62/304; 62/305
[58] Field of Search .................................. 62/259.3, 304, 62/315

[56] References Cited

U.S. PATENT DOCUMENTS

| | | | |
|---|---|---|---|
| 594,209 | 11/1897 | Mears | 62/259.3 |
| 2,335,630 | 11/1943 | Bachardy | 62/259.3 |
| 3,029,438 | 4/1962 | Henschel | 62/259.3 |
| 3,070,803 | 1/1963 | Slepicka | 62/259.3 |
| 4,356,709 | 11/1982 | Alexander | 62/530 |
| 4,566,455 | 1/1986 | Kramer | 128/380 |
| 4,753,242 | 6/1988 | Saggers | 128/380 |
| 4,998,415 | 3/1991 | Larsen | 62/259.3 |
| 5,146,757 | 9/1992 | Dearing | 62/61 |
| 5,197,292 | 3/1993 | McPherson | 62/56 |
| 5,327,585 | 7/1994 | Karlan | 2/7 |
| 5,353,605 | 10/1994 | Naaman | 62/259.3 |
| 5,365,607 | 11/1994 | Beneventon, Jr. et al. | 2/181.4 |
| 5,469,579 | 11/1995 | Tremblay et al. | 2/7 |
| 5,572,745 | 11/1996 | Mainus | 2/171.2 |
| 5,715,533 | 2/1998 | Stein | 2/7 |
| 5,867,999 | 2/1999 | Bratton et al. | 62/259.3 |

*Primary Examiner*—Henry Bennett
*Assistant Examiner*—Mark Shulman
*Attorney, Agent, or Firm*—Richard L. Miller

[57] ABSTRACT

A device for installing in a cap and dispensing a cooling medium onto the head of its wearer. The device includes a dispensing portion installed on the interior of the cap, and a cooling medium reservoir that contains and dispenses the cooling medium. The dispensing portion includes a plurality of conduits that are in fluid communication with each other, with their outer walls having a plurality of throughbores. The plurality of conduits have a shunt in fluid communication therewith. The inner walls of the plurality of conduits have thereon a layer of adhesive for attaching the plurality of conduits to the interior of the cap. The dispensing portion further includes a release sheet that cooperates with the layer of adhesive to protect the layer of adhesive prior to attaching the plurality of conduits to the interior of the cap, and as a result of its card stock, provides a simple compact configuration for the dispensing portion. The cooling medium reservoir includes a container for containing the cooling medium, a tube in fluid communication with the cooling medium and the shunt, and apparatus for selectively dispensing the cooling medium from the container, which when activated with the valve of the cooling medium reservoir open, causes the cooling medium to be drawn up through the tube, into the shunt, and through the plurality of throughbores in the plurality of conduits, onto the head of the wearer. The apparatus includes either a bulb pump or gas.

10 Claims, 2 Drawing Sheets

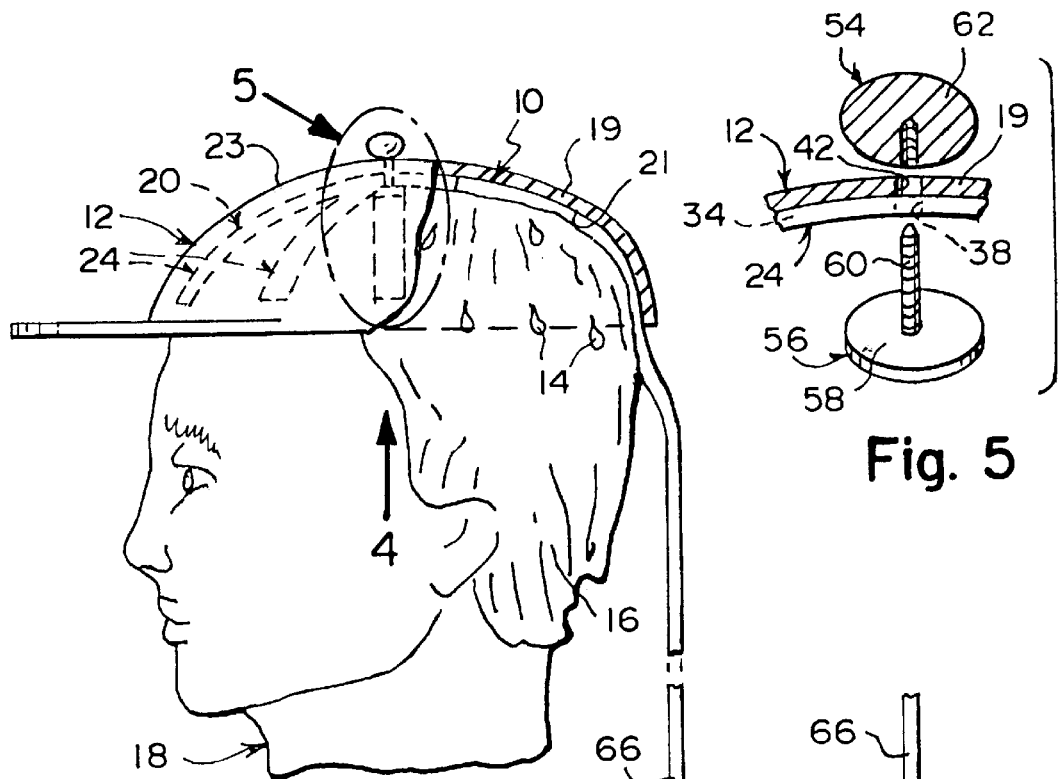
Fig. 5
Fig. 1
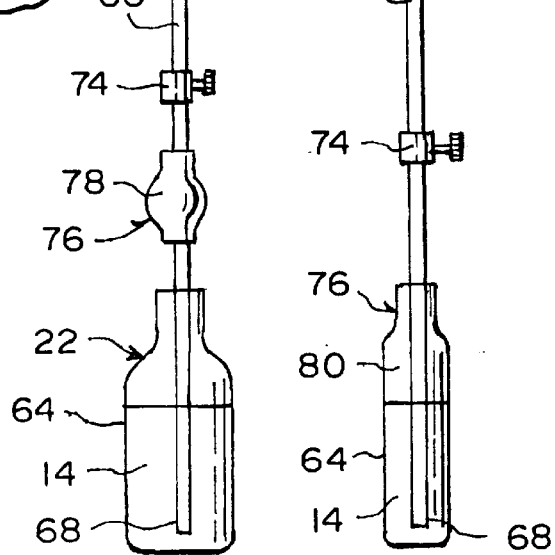
Fig. 6

APPARATUS FOR DISPENSING LIQUID ON A WEARER'S HEAD

BACKGROUND OF THE INVENTION

1. Field of the Invention

The present invention relates to a device for attaching to a cap. More particularly, the present invention relates to a device for installing in a cap and dispensing a cooling medium onto the head of its wearer.

2. Description of the Prior Art

Numerous innovations for head cooling devices have been provided in the prior art that will be described. Even though these innovations may be suitable for the specific individual purposes to which they address, however, they differ from the present invention.

A First Example, U.S. Pat. No. 5,197,292 to McPherson teaches a head wear device for cooling the wearer during athletic activity or work. The device is comprised of a cap having interior and exterior surfaces. At least one opening to at least one defined compartment chamber within the cap. The chamber is formed therewithin the interior and exterior surfaces of the cap. The chamber interior having at least one surface being of material capable of transmission of fluid from the chamber interior to the cap's interior surface.

A Second Example, U.S. Pat. No. 5,365,607 to Benevento, Jr. et al. teaches a cap utilizing evaporative cooling interior apparatus that includes a cap having a generally dome-shaped head covering portion defining an interior cavity. A plurality of elongated tapered porous liquid evaporating pads are removably secured within the cap interior in a spaced apart arrangement. A plurality of air passage channels are formed between the evaporative pads to promote air circulation about the pads within the cap interior. The pads are formed of a porous material having the capacity to absorb and retain a substantial quantity of liquid such as water. The pads preferably contact the user's head and provide a cooling effect thereon as the liquid within the porous pads evaporates.

A Third Example, U.S. Pat. No. 5,469,579 to Tremblay et al. teaches a head cooling device for mounting over a person's head, generally within a headgear or a safety helmet. The device comprises: a housing, defining a main body enclosing a generally closed pocket, for containing ice cubes therein, a mouth, at one end of the main body, and an intermediate flooring, for supporting the ice cubes inside the pocket spacedly from the mouth. Thus, the flooring remains spaced at all times from the scalp by a spacing gap. The flooring is bored at its periphery, for enabling water droplets from the melting ice cubes to escape one at a time from the pocket, freely through the spacing gap and toward and against the person's scalp. Flexible bands are used, integral to the housing, for releasably anchoring the housing to the head in generally overhanging fashion.

A Fourth Example, U.S. Pat. No. 5,572,745 to Mainus teaches a visor adapted to be worn on the head of a user that includes a brow band having a top surface and a bottom surface extending between a first end and a second end. An attachment strap extends between the first and second end to form with the brow band a headband variable in length to facilitate snug engagement on the head of the user. A sunshade extends outwardly from the bottom surface of the brow band in a fixed relationship with the headband. A first tube is included in the brow band and has a first axis extending between the first end and the second end of the brow band. Similarly, a second tube is included in the brow band and has a second axis. The first tube is disposed tangential to the second tube with the first axis generally parallel to the second axis. A water absorbent cooling material is disposed in at least one of the first and second tube to facilitate evaporation while cooling the head of the user.

It is apparent that numerous innovations for head cooling devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

Accordingly, an object of the present invention is to provide a device for installing in a cap and dispensing a cooling medium onto the head of its wearer that avoids the disadvantages of the prior art.

Another object of the present invention is to provide a device for installing in a cap and dispensing a cooling medium onto the head of its wearer that is simple and inexpensive to manufacture.

Still another object of the present invention is to provide a device for installing in a cap and dispensing a cooling medium onto the head of its wearer that is simple to use.

Briefly stated, yet another object of the present invention is to provide a device for installing in a cap and dispensing a cooling medium onto the head of its wearer. The device includes a dispensing portion installed on the interior of the cap, and a cooling medium reservoir that contains and dispenses the cooling medium. The dispensing portion includes a plurality of conduits that are in fluid communication with each other, with their outer walls having a plurality of throughbores. The plurality of conduits have a shunt in fluid communication therewith. The inner walls of the plurality of conduits have thereon a layer of adhesive for attaching the plurality of conduits to the interior of the cap. The dispensing portion further includes a release sheet that cooperates with the layer of adhesive to protect the layer of adhesive prior to attaching the plurality of conduits to the interior of the cap, and as a result of its card stock, provides a simple compact configuration for the dispensing portion. The cooling medium reservoir includes a container for containing the cooling medium, a tube in fluid communication with the cooling medium and the shunt, and apparatus for selectively dispensing the cooling medium from the container, which when activated with the valve of the cooling medium reservoir open, causes the cooling medium to be drawn up through the tube, into the shunt, and through the plurality of throughbores in the plurality of conduits, onto the head of the wearer. The apparatus includes either a bulb pump or gas.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawings.

BRIEF DESCRIPTION OF THE DRAWING

The figures on the drawing are briefly described as follows:

FIG. 1 is a diagrammatic side elevational view of the present invention installed in a cap and dispensing a cooling medium onto the head of a wearer;

FIG. 5 is an enlarged diagrammatic perspective view of the area generally enclosed by the dotted ellipse identified by arrow 5 in FIG. 1; and FIG. 6 is a diagrammatic side elevational view of an alternate embodiment for the cooling medium reservoir of the present invention.

LIST OF REFERENCE NUMERALS UTILIZED IN THE DRAWING

Figure 4:
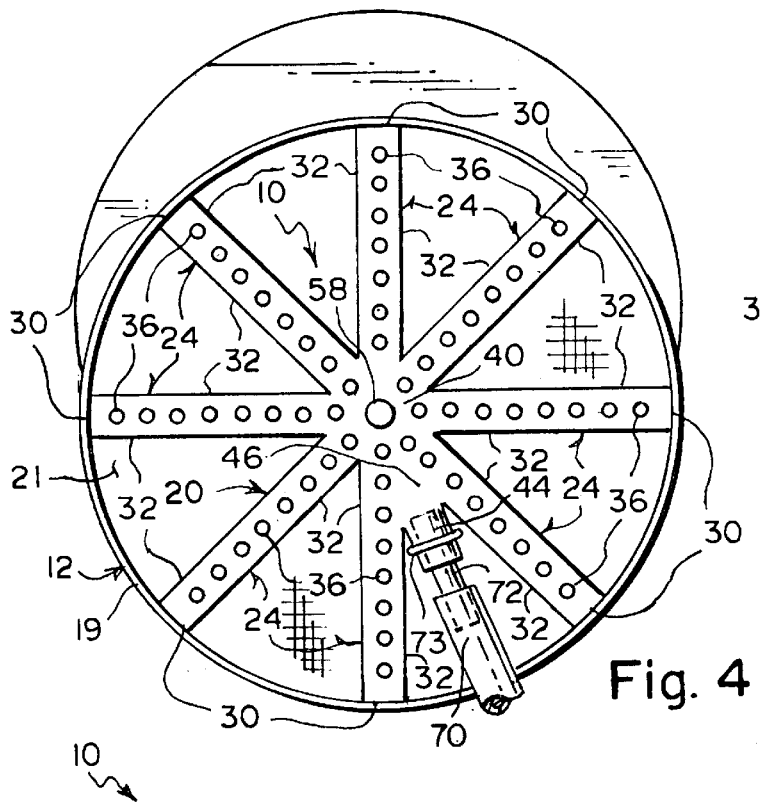
FIG. 4 is a diagrammatic bottom plan view taken generally in the direction of arrow 4 in FIG. 1 of the present invention installed in the cap.

10—device for installing in a cap and dispensing a cooling medium onto the head of its wearer of the present invention
12—cap
14—cooling medium
16—head of wearer 18
18—wearer
19—head engaging portion of cap 12
21—interior of head engaging portion 19 of cap 12
20—dispensing portion for installation on interior 21 of cap 12
22—cooling medium reservoir for containing and dispensing cooling medium 14
23—exterior of head engaging portion 19 of cap 12
24—plurality of conduits of dispensing portion 20
26—inner walls of plurality of conduits 24 of dispensing portion 20 for radially attaching to interior 21 of head engaging portion 19 of cap 12
28—outer walls of plurality of conduits 24 of dispensing portion 20 for facing head 16 of wearer 18
30—terminal ends of plurality of conduits 24 of dispensing portion 20
32—longitudinal edges of plurality of conduits 24 of dispensing portion 20
34—plurality of passageways defined between inner walls 26 of plurality of conduits 24 of dispensing portion 20 and outer walls 28 of plurality of conduits 24 of dispensing portion 20
36—plurality of throughbores in outer walls 28 of plurality of conduits 24 of dispensing portion 20
38—common throughbore in point of intersection 40 of plurality of conduits 24 of dispensing portion 20
40—point of intersection of plurality of conduits 24 of dispensing portion 20
42—center hole in head engaging portion 19 of cap 12
44—shunt at point of intersection of pair of conduits of plurality of conduits 24 of dispensing portion 20
46—point of intersection of pair of conduits of plurality of conduits 24 of dispensing portion 20
48—passageway in shunt 44 of plurality of conduits 24 of dispensing portion 20
50—layer of adhesive on inner walls 26 of plurality of conduits 24 of dispensing portion 20 for radially attaching plurality of conduits 24 of dispensing portion 20 to interior 21 of head engaging portion 19 of cap 12
52—release sheet of dispensing portion 20
54—bead portion of dispensing portion 20 for further securing dispensing portion 20 to interior 21 of head engaging portion 19 of cap 12
56—male part of bead portion 54 of dispensing portion 20
58—base of male part 56 of bead portion 54 of dispensing portion 20
60—threaded shank of male part 56 of bead portion 54 of dispensing portion 20
62—female part of bead portion 54 of dispensing portion 20
64—container of cooling medium reservoir 22 for containing cooling medium 14 and being carried with wearer 18
66—tube of cooling medium reservoir 22
68—one end of tube 66 of cooling medium reservoir 22
70—other end of tube 66 of cooling medium reservoir 22
72—sleeve of cooling medium reservoir 22
73—clamp ring of cooling medium reservoir 22
74—valve of cooling medium reservoir 22 for controlling cooling medium 14 being dispensed from container 62 of cooling medium reservoir 22
76—dispensing apparatus of cooling medium reservoir 22 for selectively dispensing cooling medium 14 from container 62 of cooling medium reservoir 22
78—bulb pump of dispensing apparatus 76 of cooling medium reservoir 22
80—gas of dispensing apparatus 76 of cooling medium reservoir 22

DETAILED DESCRIPTION OF THE PREFERRED EMBODIMENT

Referring now to the figures, in which like numerals indicate like parts, and particularly to FIG. 1, the device for installing in a cap and dispensing a cooling medium onto the head of its wearer of the present invention is shown generally at 10 for installing in a cap 12 and dispensing a cooling medium 14 onto the head 16 of its wearer 18, wherein the cap 12 has a head engaging portion 19 for engaging the head 16 of the wearer and which has an interior 21 and an exterior 23.

It is to be understood that the cooling medium 14 is typically cold water for illustrative purposes only, but is not to be considered limited thereto.

The configuration of the device for installing in a cap and dispensing a cooling medium onto the head of its wearer 10 can best be seen in FIGS. 1–6, and as such will be discussed with reference thereto.

As shown in FIG. 1, the device for installing in a cap and dispensing a cooling medium onto the head of its wearer 10 comprises a dispensing portion 20 for installation on the interior 21 of the cap 12 and a cooling medium reservoir 22 in fluid communication with the dispensing portion 20 for containing and dispensing the cooling medium 14.

Figure 3:
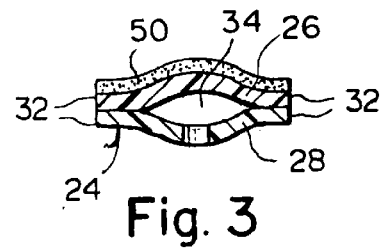
FIG. 3 is an enlarged cross sectional view taken on line 3—3 in FIG. 2.
Figure 2:
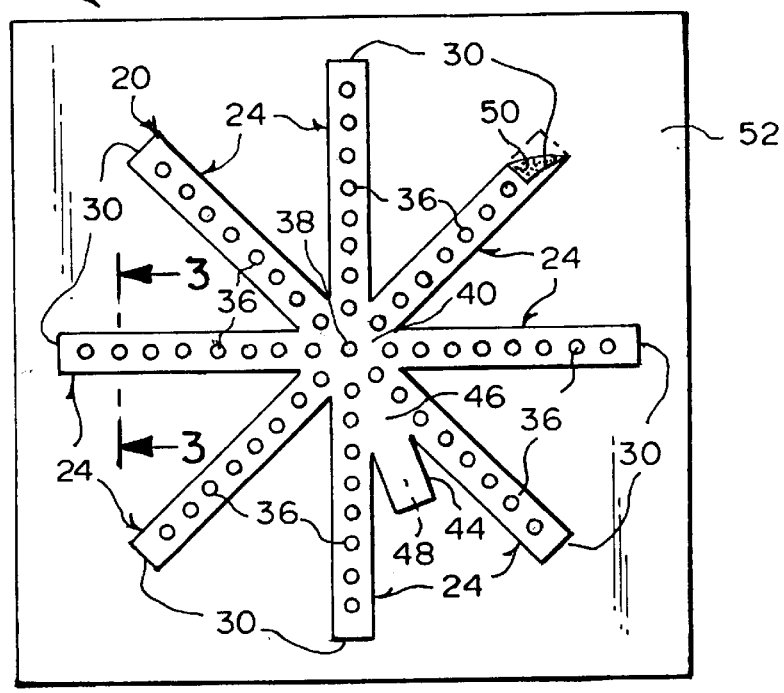
FIG. 2 is a diagrammatic bottom plan view of the present invention prior to installation in the cap.

As shown in FIGS. 2–4, the dispensing portion 20 comprises a plurality of conduits 24 that are flexible, elongated, slender, radially-oriented, and in fluid communication with each other, and have inner walls 26 for radially attaching to the interior 21 of the head engaging portion 19 of the cap 12, outer walls 28 for facing the head 16 of the wearer 18, and terminal ends 30 that are sealed.

As shown in FIG. 3, the outer walls 28 of the plurality of conduits 24 of the dispensing portion 20 are affixed to respective inner walls 26 of the plurality of conduits 24 of the dispensing portion 20, only along their longitudinal edges 32 and their terminal ends 30, and thereby defining a plurality of passageways 34 therebetween.

As shown in FIGS. 2 and 4, the outer walls 28 of the plurality of conduits 24 of the dispensing portion 20 have a plurality of throughbores 36 therethrough that are spaced longitudinally therealong and which are in fluid communication with the plurality of passageways 34 in the plurality of conduits 24 of the dispensing portion 20.

As shown in FIGS. 2 and 4, the plurality of conduits 24 of the dispensing portion 20 have a common throughbore 38 therethrough, at their point of intersection 40, which is sealed against fluid communication with, but does not obstruct, the plurality of passageways 34 in the plurality of conduits 24 of the dispensing portion 20, and is for alignment with a center hole 42 in the head engaging portion 19 of the cap 12, if such is present.

As shown in FIGS. 2 and 4, the plurality of conduits 24 of the dispensing portion 20 further have a shunt 44 disposed between, and in fluid communication with, a pair of conduits of the plurality of conduits 24 of the dispensing portion 20, at their point of intersection 46, and whose passageway 48 is defined by continuation of the outer walls 28 of the plurality of conduits 24 of the dispensing portion 20 and the respective inner walls 26 of the plurality of conduits 24 of the dispensing portion 20.

As shown in FIGS. 2 and 3, the inner walls 26 of the plurality of conduits 24 of the dispensing portion 20 have thereon a layer of adhesive 50 for radially attaching the plurality of conduits 24 of the dispensing portion 20 to the interior 21 of the head engaging portion 19 of the cap 12.

As shown in FIG. 2, the dispensing portion 20 further comprises a release sheet 52 that is generally square and of card stock and somewhat larger than the plurality of conduits 24 of the dispensing portion 20.

As shown in FIG. 2, the release sheet 52 of the dispensing portion 20 cooperates with the layer of adhesive 50 to protect the layer of adhesive 50 prior to radially attaching the plurality of conduits 24 of the dispensing portion 20 to the interior 21 of the head engaging portion 19 of the cap 12, and as a result of its card stock provides a simple compact configuration for the dispensing portion 20.

As shown in FIG. 2, the release sheet 52 of the dispensing portion 20 extends past the plurality of conduits 24 of the dispensing portion 20 which allows the plurality of conduits 24 of the dispensing portion 20 to be simply peeled thereoff and attached radially to the interior 21 of the head engaging portion 19 of the cap 12 during installation.

As shown in FIG. 5, the dispensing portion 20 further comprises a bead portion 54 for further securing the dispensing portion 20 to the interior 21 of the head engaging portion 19 of the cap 12, if the cap 12 has the center hole 42 in the head engaging portion 19 of the cap 12.

As shown in FIG. 5, the bead portion 54 of the dispensing portion 20 comprises a male part 56 that comprises a base 58 that is disk-shaped and large than the common throughbore 38 in the plurality of conduits 24 of the dispensing portion 20, and which engages the point of intersection 40 of the plurality of conduits 24 of the dispensing portion 20, from the outer walls 28 thereof.

As shown in FIG. 5, the male part 56 of the bead portion 54 of the dispensing portion 20 further comprises a threaded shank 60 that extends upwardly from the base 58 of the male part 56 of the bead portion 54 of the dispensing portion 20, through the common throughbore 38 in the plurality of conduits 24 of the dispensing portion 20, and through the center hole 42 in the head engaging portion 19 of the cap 12.

As shown in FIG. 5, the bead portion 54 of the dispensing portion 20 further comprises a female part 62 that is disk-shaped and larger than the center hole 42 in the head engaging portion 19 of the cap 12, and which engages the exterior 23 of the head engaging portion 19 of the cap 21, while threadably engaging the threaded shank 60 of the male part 56 of the bead portion 54 of the dispensing portion 20, and thereby securingly sandwiching both the head engaging portion 19 of the cap 12 and the plurality of conduits 24 of the dispensing portion 20 between itself and the base 58 of the male part 56 of the bead portion 54 of the dispensing portion 20.

As shown in FIG. 1, the cooling medium reservoir 22 comprises a container 64 for containing the cooling medium 14 and being carried with the wearer 18.

As shown in FIGS. 1 and 4, the cooling medium reservoir 22 further comprises a tube 66 that is flexible, and is at one end 68 in fluid communication with the cooling medium 14 in the container 64 of the cooling medium reservoir 22, and at the other end 70 in fluid communication with the shunt 44 of the plurality of conduits 24 of the dispensing portion 20.

As shown in FIG. 4, the other end 70 of the tube 66 of the cooling medium reservoir 22 is maintained in fluid communication with the shunt 44 of the plurality of conduits 24 of the dispensing portion 20 by a sleeve 72 that securingly enters both the other end 70 of the tube 66 of the cooling medium reservoir 22 and the shunt 44 of the plurality of conduits 24 of the dispensing portion 20, with a clamp ring 73 replaceable therearound.

As shown in FIG. 1, the cooling medium reservoir 22 further comprises a valve 74 in fluid communication with the tube 66 of the cooling medium reservoir 22 for controlling the cooling medium 14 being dispensed from the container 62 of the cooling medium reservoir 22.

As shown in FIG. 1, the cooling medium reservoir 22 further comprises dispensing apparatus 76 for selectively dispensing the cooling medium 14 from the container 62 of the cooling medium reservoir 22, which when activated with the valve 74 of the cooling medium reservoir 22 open, causes the cooling medium 14 in the container 64 of the cooling medium reservoir 22 to be drawn up through the tube 66 of the cooling medium reservoir 22, into the shunt 44 of the plurality of conduits 24 of the dispensing portion 22, through the plurality of conduits 24 of the dispensing portion 22, and through the plurality of throughbores 36 in the outer walls 28 of the plurality of conduits 24 of the dispensing portion 20, onto the head 16 of the wearer 18.

As shown in FIG. 1, in one embodiment, the dispensing apparatus 76 of the cooling medium reservoir 22 comprises a bulb pump 78 in fluid communication with the tube 66 of the cooling medium reservoir 22, between the container 64 of the cooling medium reservoir 22 and the valve 74 of the cooling medium reservoir 22, with the valve 74 of the cooling medium reservoir 22 preventing dispensing of the cooling medium 14 from the container 62 of the cooling medium reservoir 22 if the bulb pump 78 of the dispensing apparatus 76 of the cooling medium reservoir 22 is inadvertently squeezed.

As shown in FIG. 1, in another embodiment, the dispensing apparatus 76 of the cooling medium reservoir 22 comprises a gas 80 in the container 64 of the cooling medium reservoir 22, above the cooling medium 14 in the container 62 of the cooling medium reservoir 22, and when the container 62 of the cooling medium reservoir 22 is shook the gas 80 of the dispensing apparatus 76 of the cooling medium reservoir 22 mixes with the cooling medium 14 in the container 62 of the cooling medium reservoir 22 and increases its pressure to form a high pressured cooling medium, with the valve 74 of the cooling medium reservoir 22 preventing dispensing of the high pressure cooling medium from the container 62 of the cooling medium reservoir 22 if the container 62 of the cooling medium reservoir 22 is inadvertently shook.

It will be understood that each of the elements described above, or two or more together, may also find a useful application in other types of constructions differing from the types described above.

While the invention has been illustrated and described as embodied in a device for installing in a cap and dispensing a liquid onto the head of its wearer, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A device for installing in a cap and dispensing a cooling medium onto the head of its wearer, wherein the cap has a head engaging portion for engaging the head of the wearer and which has an interior and an exterior, said device comprising:
   a) a dispensing portion for installation on the interior of the cap; and
   b) a cooling medium reservoir in fluid communication with said dispensing portion for containing and dispensing the cooling medium, wherein said dispensing portion comprises a plurality of conduits that are flexible, elongated, slender, radially-oriented, and in fluid communication with each other, and have inner walls for radially attaching to the interior of the head engaging portion of the cap, outer walls for facing the head of the wearer, and terminal ends that are sealed, wherein said outer walls of said plurality of conduits of said dispensing portion are affixed to respective inner walls of said plurality of conduits of said dispensing portion, only along their longitudinal edges and their terminal ends, and thereby defining a plurality of passageways therebetween, wherein said inner walls of said plurality of conduits of said dispensing portion have thereon a layer of adhesive for radially attaching said plurality of conduits of said dispensing portion to the interior of the head engaging portion of the cap, wherein said dispensing portion further comprises a release sheet that is generally square and of card stock and somewhat larger than said plurality of conduits of said dispensing portion.

2. The device as defined in claim 1, wherein said release sheet of said dispensing portion cooperates with said layer of adhesive to protect said layer of adhesive prior to radially attaching said plurality of conduits of said dispensing portion to the interior of the head engaging portion of the cap, and as a result of its card stock, provides a simple compact configuration for said dispensing portion.

3. The device as defined in claim 1, wherein said release sheet of said dispensing portion extends past said plurality of conduits of said dispensing portion which allows said plurality of conduits of said dispensing portion to be simply peeled thereoff and attached radially to the interior of the head engaging portion of the cap during installation.

4. A device for installing in a cap and dispensing a cooling medium onto the head of its wearer, wherein the cap has a head engaging portion for engaging the head of the wearer and which has an interior and an exterior, said device comprising:
   a) a dispensing portion for installation on the interior of the cap; and
   b) a cooling medium reservoir in fluid communication with said dispensing portion for containing and dispensing the cooling medium, wherein said dispensing portion comprises a plurality of conduits that are flexible, elongated, slender, radially-oriented, and in fluid communication with each other, and have inner walls for radially attaching to the interior of the head engaging portion of the cap, outer walls for facing the head of the wearer, and terminal ends that are sealed, wherein said outer walls of said plurality of conduits of said dispensing portion are affixed to respective inner walls of said plurality of conduits of said dispensing portion, only along their longitudinal edges and their terminal ends, and thereby defining a plurality of passageways therebetween, wherein said plurality of conduits of said dispensing portion have a common throughbore therethrough, at their point of intersection, which is sealed against fluid communication with, but does not obstruct, said plurality of passageways in said plurality of conduits of said dispensing portion, and is for alignment with a center hole in the head engaging portion of the cap, if such is present, wherein said dispensing portion comprises a bead portion for further securing said dispensing portion to the interior of the head engaging portion of the cap, if the cap has the center hole in the head engaging portion of the cap.

5. The device as defined in claim 4, wherein said bead portion of said dispensing portion comprises a male part that comprises a base that is disk-shaped and larger than said common throughbore in said plurality of conduits of said dispensing portion, and which engages said point of intersection of said plurality of conduits of said dispensing portion, from said outer walls thereof.

6. The device as defined in claim 5, wherein said male part of said bead portion of said dispensing portion further comprises a threaded shank that extends upwardly from said base of said male part of said bead portion of said dispensing portion, through said common throughbore in said plurality of conduits of said dispensing portion, and through the center hole in the head engaging portion of the cap.

7. The device as defined in claim 13, wherein said bead portion of said dispensing portion further comprises a female part that is disk-shaped and larger than the center hole in the head engaging portion of the cap, and which engages the exterior of the head engaging portion of the cap, while threadably engaging said threaded shank of said male part of said bead portion of said dispensing portion, and thereby securingly sandwiching both the head engaging portion of the cap and said plurality of conduits of said dispensing portion between itself and said base of said male part of said bead portion of said dispensing portion.

8. A device for installing in a cap and dispensing a cooling medium onto the head of its wearer, wherein the cap has a head engaging portion for engaging the head of the wearer and which has an interior and an exterior, said device comprising:
   a) a dispensing portion for installation on the interior of the cap; and
   b) a cooling medium reservoir in fluid communication with said dispensing portion for containing and dispensing the cooling medium, wherein said dispensing portion comprises a plurality of conduits that are flexible, elongated, slender, radially-oriented, and in fluid communication with each other, and have inner walls for radially attaching to the interior of the head engaging portion of the cap, outer walls for facing the head of the wearer, and terminal ends that are sealed, wherein said outer walls of said plurality of conduits of said dispensing portion are affixed to respective inner walls of said plurality of conduits of said dispensing portion, only along their longitudinal edges and their terminal ends, and thereby defining a plurality of passageways therebetween, wherein said outer walls of said plurality of conduits of said dispensing portion have a plurality of throughbores therethrough that are spaced longitudinally therealong and which are in fluid communication with said plurality of passageways in said plurality of conduits of said dispensing portion, wherein said plurality of conduits of said dispensing portion have a shunt disposed between, and in fluid communication with, a pair of conduits of said plurality of conduits of said dispensing portion, at their point of intersection, and whose passageway is defined by continuation of said outer walls of said plurality of conduits of said dispensing portion and said respective inner walls of said plurality of conduits of said dispensing portion, wherein said cooling medium reservoir comprises a container for containing the cooling medium and being carried with the wearer, wherein said cooling medium reservoir further comprises a tube that is flexible, and is at one end, in fluid communication with the cooling medium in said container of said cooling medium reservoir, and at the other end, is in fluid communication with said shunt of said plurality of conduits of said dispensing portion, wherein said other end of said tube of said cooling medium reservoir is maintained in fluid communication with said shunt of said plurality of conduits of said dispensing portion by a sleeve that securingly enters both said other end of said tube of said cooling medium reservoir and said shunt of said plurality of conduits of said dispensing portion, with a clamp ring replaceable therearound.

9. A device for installing in a cap and dispensing a cooling medium onto the head of its wearer, wherein the cap has a head engaging portion for engaging the head of the wearer and which has an interior and an exterior, said device comprising:

a) a dispensing portion for installation on the interior of the cap; and b) a cooling medium reservoir in fluid communication with said dispensing portion for containing and dispensing the cooling medium, wherein said dispensing portion comprises a plurality of conduits that are flexible, elongated, slender, radially-oriented, and in fluid communication with each other, and have inner walls for radially attaching to the interior of the head engaging portion of the cap, outer walls for facing the head of the wearer, and terminal ends that are sealed, wherein said outer walls of said plurality of conduits of said dispensing portion are affixed to respective inner walls of said plurality of conduits of said dispensing portion, only along their longitudinal edges and their terminal ends, and thereby defining a plurality of passageways therebetween, wherein said outer walls of said plurality of conduits of said dispensing portion have a plurality of throughbores therethrough that are spaced longitudinally therealong and which are in fluid communication with said plurality of passageways in said plurality of conduits of said dispensing portion, wherein said plurality of conduits of said dispensing portions have a shunt disposed between, and in fluid communication with, a pair of conduits of said plurality of conduits of said dispensing portion, at their point of intersection, and whose passageway is defined by continuation of said outer walls of said plurality of conduits of said dispensing portion and said respective inner walls of said plurality of conduits of said dispensing portion, wherein said cooling medium reservoir comprises a container for containing the cooling medium and being carried with the wearer, wherein said cooling medium reservoir further comprises a tube that is flexible, and is at one end, in fluid communication with the cooling medium in said container of said cooling medium reservoir, and at the other end, is in fluid communication with said shunt of said plurality of conduits of said dispensing portion, wherein said cooling medium reservoir further comprises a valve in fluid communication with said tube of said cooling medium reservoir for controlling the cooling medium being dispensed from said container of said cooling medium reservoir, wherein said cooling medium reservoir further comprises means for selectively dispensing the cooling medium from said container of said cooling medium reservoir, which when activated with said valve of said cooling medium reservoir open, causes the cooling medium in said container of said cooling medium reservoir to be drawn up through said tube of said cooling medium reservoir, into said shunt of said plurality of conduits of said dispensing portion, through said plurality of conduits of said dispensing portion, and through said plurality of throughbores in said outer walls of said plurality of conduits of said dispensing portion, onto the head of the wearer, wherein said means of said cooling medium reservoir includes a bulb pump in fluid communication with said tube of said cooling medium reservoir, between said container of said cooling medium reservoir and said valve of said cooling medium reservoir, with said valve of said cooling medium reservoir preventing dispensing of the cooling medium from said container of said cooling medium reservoir if said bulb pump of said means of said cooling medium reservoir is inadvertently squeezed.

10. The device as defined in claim 9, wherein said means of said cooling medium reservoir includes a gas in said container of said cooling medium reservoir, above the cooling medium in said container of said cooling medium reservoir, and when said container of said cooling medium reservoir is shook, said gas of said means of said cooling medium reservoir mixes with the cooling medium in said container of said cooling medium reservoir and increases its pressure to form a high pressured cooling medium, with said valve of said cooling medium reservoir preventing dispensing of said high pressure cooling medium from said container of said cooling medium reservoir if said container of said cooling medium reservoir is inadvertently shook.

* * * * *